United States Patent
Hurlimann et al.

(10) Patent No.: US 10,444,397 B2
(45) Date of Patent: Oct. 15, 2019

(54) NMR WELL LOGGING INSTRUMENT AND METHOD WITH SYNTHETIC APERTURES

(71) Applicant: Schlumberger Technology Corporation, Sugar Land, TX (US)

(72) Inventors: Martin Hurlimann, Newton, MA (US); Irfan Bulu, Boston, MA (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 183 days.

(21) Appl. No.: 15/363,905

(22) Filed: Nov. 29, 2016

(65) Prior Publication Data

US 2018/0149765 A1    May 31, 2018

(51) Int. Cl.
| | |
|---|---|
| *G01V 3/32* | (2006.01) |
| *G01R 33/50* | (2006.01) |
| *G01N 24/08* | (2006.01) |
| *G01R 33/3415* | (2006.01) |

(52) U.S. Cl.
CPC .............. *G01V 3/32* (2013.01); *G01N 24/081* (2013.01); *G01R 33/3415* (2013.01); *G01R 33/50* (2013.01)

(58) Field of Classification Search
CPC .... G01V 3/32; G01N 24/081; G01R 33/3415; G01R 33/50
USPC ........................................................ 324/303
See application file for complete search history.

(56) References Cited

U.S. PATENT DOCUMENTS

| | | | |
|---|---|---|---|
| 4,710,713 A | 12/1987 | Strickman | |
| 5,629,623 A | 5/1997 | Sezginer et al. | |
| 6,121,773 A | 9/2000 | Taicher et al. | |
| 6,140,818 A | 10/2000 | Hurlimann | |
| 6,268,726 B1 | 7/2001 | Prammer et al. | |

(Continued)

FOREIGN PATENT DOCUMENTS

EP         0459064 A1    12/1991

OTHER PUBLICATIONS

International Search Report and Written Opinion issued in the related PCT Application PCT/US2017/063627 dated Mar. 14, 2018 (18 pages).

(Continued)

*Primary Examiner* — Jermele M Hollington
*Assistant Examiner* — Suresh K Rajaputra
(74) *Attorney, Agent, or Firm* — Trevor G. Grove (57) ABSTRACT

An apparatus for measuring nuclear magnetic resonance (NMR) properties of subsurface formations includes a magnet for pre-polarizing nuclear spins in the formations. A plurality of transmitter antennas is spaced apart along a length of the apparatus. The apparatus includes at least one of a receiver circuit selectively coupled to at least one of the plurality of transmitter antennas and a separate receiver antenna. The apparatus includes circuitry for applying radio frequency current pulses selectively to each of the plurality of transmitter antennas such that during a NMR measurement sequence while the apparatus is moving substantially only those of the plurality of transmitter antennas having radio frequency current pulses applied thereto are disposed longitudinally along a same region of interest in the subsurface formations.

23 Claims, 7 Drawing Sheets

(56) References Cited

U.S. PATENT DOCUMENTS

| | | | |
|---|---|---|---|
| 6,285,901 B1 | 9/2001 | Taicher et al. | |
| 6,637,524 B2 | 10/2003 | Kruspe et al. | |
| 6,825,659 B2 * | 11/2004 | Prammer | G01V 3/32 324/300 |
| 6,838,875 B2 | 1/2005 | Freedman | |
| 7,733,086 B2 * | 6/2010 | Prammer | G01V 3/32 324/300 |
| 2002/0153888 A1 | 10/2002 | Kruspe et al. | |
| 2002/0171421 A1 | 11/2002 | Forgang et al. | |
| 2007/0257679 A1 | 11/2007 | Fanini et al. | |
| 2008/0174313 A1 | 7/2008 | Ganesan | |
| 2009/0018775 A1 | 1/2009 | Tabarovsky et al. | |
| 2011/0068787 A1 * | 3/2011 | Freedman | E21B 7/046 324/303 |
| 2013/0093422 A1 * | 4/2013 | Morys | G01V 3/32 324/303 |
| 2017/0254916 A1 * | 9/2017 | Yu | E21B 17/1078 |

OTHER PUBLICATIONS

Freeman, "Advances in NMR Logging", JPT, SPE 89177, Jan. 2006 pp. 60-66.
International Preliminary Report on Patentability issued in the related PCT Application PCT/US2017/063627 dated Jun. 13, 2019 (14 pages).

* cited by examiner

NMR WELL LOGGING INSTRUMENT AND METHOD WITH SYNTHETIC APERTURES

CROSS REFERENCE TO RELATED APPLICATIONS

Not Applicable

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable.

BACKGROUND

This disclosure relates to the field of nuclear magnetic resonance (NMR) well logging apparatus and methods. More specifically, the disclosure relates to methods and apparatus for NMR well logging that can make accurate measurements of NMR properties of formations surrounding a well at greater speed of motion of the well logging instrument without degradation of the measurements as a result of motion of the well logging instrument.

NMR-based measurement of the fractional volume of pore space (porosity) of subsurface formations, which is substantially independent of the rock mineral composition (matrix) of the subsurface formations, has been widely accepted. In complex environments, where the matrix properties are not well known, NMR measurements may provide more accurate porosities than other well logging instruments used to determine porosity. In addition, NMR transverse relaxation time ($T_2$) distributions may provide additional information about bound-fluid porosities and reservoir quality. Notwithstanding the superior quality of NMR porosity measurements, NMR well logging remains a niche service. One reason that has hindered NMR well logging from becoming a more widely used service for determination of subsurface formation properties is the relatively slow logging speeds that may be used with NMR instruments known in the art compared to that of other porosity tools.

NMR-determined porosities and $T_2$ distributions are adversely affected by speed of motion of the well logging instrument along a wellbore. Speed effects are more problematic with NMR measurements because of the fact that NMR measurements take a relatively long time (e.g., seconds) compared to other logging tool measurements. Logging speeds for NMR well logging instruments known in the art are relatively slow, e.g., typically in the range from 300 to 900 feet per hour depending on the logging environment and the specific application.

NMR well logging measurements are based on the application of a static magnetic field $B_0$ to formations adjacent a wellbore to polarize the nuclear magnetic spins of susceptible nuclei (e.g., hydrogen) along a selected direction and applying on-resonance radio-frequency magnetic fields $B_1$ to manipulate the magnetization (for instance by generating transverse magnetization and then repeatedly refocusing the transverse magnetization). In a well logging instrument, the spatial distributions of the two types of magnetic fields $B_0$ and $B_1$, are optimized to localize a "sensitive region", i.e., a region where nuclear magnetic resonance is induced in the susceptible nuclei, in the formation. Many types of well logging instruments are moved along the wellbore while making measurements of selected formation properties. Motion of an NMR well logging instrument relative to the formation affects the NMR measurements because both the static ($B_0$) and RF ($B_1$) magnetic fields will have time dependence. These effects can be modeled in detail by using the Bloch equation with the relevant time dependent fields.

To obtain a general understanding of logging instrument motion effects on NMR measurements, it is useful to categorize the motion effects into three distinct effects:
1. Incomplete polarization;
2. Enhanced signal decay; and
3. Spoiling of longitudinal magnetization prior to measurement.

To perform a quantitative NMR measurement, the nuclear spins have to be first polarized to a known longitudinal magnetization, such as the thermal magnetization. RF magnetic field pulses are then applied to convert the longitudinal magnetization to transverse magnetization. The transverse magnetization induces RF energy that can be measured, for example, by inductive detection in an antenna. Ideally, the initial polarization is obtained by exposing the formation to a static magnetic field of strength $B_0$ for a time that is relatively long with respect to the longitudinal relaxation time, $T_1$ This way, the nuclear magnetic spins reach thermal equilibrium where the magnetization is exactly proportional to the formation porosity and the hydrogen index, with a known proportionality factor that depends only on the strength of the static magnetic field $B_0$ and the temperature T. With a short-length well logging instrument that is moving along the wellbore, these condition can become difficult to fulfill when the values of $T_1$ become longer than a few seconds.

This problem has been addressed in one aspect by adding a long prepolarization magnet in front of the measurement section, as described, for example in U.S. Pat. No. 6,140,818, "NMR logging tool and method for fast logging", issued at Oct. 31, 2000.

As long as the prepolarization section (i.e., a permanent magnet or DC electromagnet) is long compared to $vT_1$, for even the longest expected longitudinal relaxation time, all nuclear magnetic spins are fully polarized. Here v is the instrument speed during measurement.

The NMR signal induced after applying the RF pulses is generally designed to be proportional to the initial longitudinal magnetization. For a quantitative measurement, it is important that RF magnetic field pulses do not perturb the longitudinal magnetization before the intended measurement. This has led to the concept of non-overlapping measurements, also disclosed in the above mentioned '818 patent.

In a simple implementation, the RF magnetic field pulse sequence consists of an initial 90° reorienting pulse followed by a selected length "string" of 180° refocusing pulses. The RF magnetic field pulses may be induced by applying selected duration and amplitude RF electric current at the Larmor frequency of the susceptible nuclei in the sensitive region through an antenna. The same antenna may be connected to receiving circuits between successive RF pulses to detect the amplitude of nuclear magnetization spin echoes. In some implementations a separate antenna may be used for detecting the NMR signals. Such sequence is known as a Carr-Purcell-Meiboom-Gill (CPMG) RF pulse sequence In this case, it may be assumed that the duration of the CPMG pulse sequence is no longer than Lant/v, i.e., the duration required for the logging instrument to move the length of the antenna. The initial 90° RF magnetic field pulse tips the longitudinal magnetization into the transverse plane and the subsequent string of 180° RF magnetic field pulses act to refocus the nuclear magnetic spins to keep the transverse magnetization coherent. As the instrument and its antenna(s) move upwardly, the spins in the formation below the bottom of the antenna(s) do not experience the 180° refocusing pulses anymore, and the magnetization decays. Tmeas may denote the duration after the initial 90° RF magnetic field pulse that the formation experiences the 180° refocusing pulses. This is the effective measurement time. To a first order, Tmeas is given by Tmeas=(x/Lant) (v/Lant) where x is the distance along the formation from the position where the bottom of the antenna was disposed at the time of the 90° RF magnetic field pulse. This assumes that the duration of the CPMG pulse sequence is 1/(v/Lant). Tmeas sets the limit of the longest transverse $T_2$ relaxation time that can be accurately determined.

As the logging instrument moves upwardly, the 180° refocusing pulses start to act on nuclear magnetic spins of the formation that have not been affected by the initial 90° pulse of the CPMG sequence. Consequently, the magnetization of these spins will be strongly perturbed and they will deviate from the thermal equilibrium, but they will not generate a coherent NMR signal. This region of disturbed magnetization is known as a "hole-burning" region.

In order to be able to start a subsequent CPMG sequence, the instrument has to move a distance Lant after the end of the current CPMG sequence in order to encounter spins in the formation that have not been disturbed yet from equilibrium by the RF magnetic field pulses. As a consequence, no NMR information can be obtained from this region and the porosity sensitivity of the instrument to this region is essentially zero.

A simple modification that can increase the fraction of the formation which is measured by the NMR instrument with high porosity sensitivity may be obtained by decreasing the duration of the CPMG sequence (i.e., decreasing the number of 180° refocusing pulses). One may reduce the duration of the CPMG pulse sequence by a factor of ε. This has the advantage that the length of the hole-burning region is reduced from Lant to around εLant. Therefore, the fraction of the formation that can be investigated increases from about 50% to around 1/(1+ε). However, this comes at a cost of reduced effective measurement time that is now a maximum of only εLant/v. This greatly limits the $T_2$ resolution as compared to the standard implementation described above. The fraction of time that RF refocusing magnetic field pulses are applied to the formation decreases from 50% to ε/(1+ε).

One possible solution to increase the porosity sensitivity over the formation without reducing the effective measurement time is based on multi-frequency operation of the NMR instrument. The carrier frequency f of subsequent CPMG sequences is systematically switched between at least two frequencies, e.g. from f1 to f2. Changing the frequency changes the depth of investigation (DOI) of the sensitive region based on the Larmor condition $B_0(r=DOI)=2\pi f/\gamma$. By switching the DOI, the perturbed region from the previous CPMG measurement sequence can be avoided. With this approach, most of the formation along the borehole can be investigated. It requires that the difference between RF frequencies (and therefore DOI) is large enough to avoid any interference. The systematic variation of DOI can complicate the interpretation when invasion or formation damage is present. This approach also leads to a systematic variation in signal to noise ratio because it will depend on DOI. Note that the effective measurement time Tmeas still varies across the formation.

Another possible solution to overcome the motion effects for NMR measurements was proposed by Kruspe et al., U.S. Pat. No. 6,637,524, "Non-rotating sensor assembly for measurement-while-drilling application", Oct. 28, 2003. In this patent, it was suggested to build a logging device where the NMR sensor is built on a slidable sleeve that is mechanically separate from the rest of the bottom-hole assembly. This allows in principle to keep the NMR sensor temporally fixed relative to the formation and conduct an NMR measurement. After the measurement is complete, the NMR sensor is then repositioned to a different part of the formation that has not been affected by the RF pulses of the previous measurement sequence and the process is repeated. This approach requires a complicated mechanical design and is therefore associated with high cost and low reliability. The method and apparatus described in the '524 patent does not appear to have been developed successfully for commercial services.

SUMMARY

An apparatus for determining NMR properties of subsurface formations according to one aspect of the present disclosure includes a magnet for pre-polarizing nuclear spins in the formations. A plurality of transmitter antennas is spaced apart along a length of the apparatus. The apparatus includes at least one of a receiver circuit selectively coupled to at least one of the plurality of transmitter antennas and a separate receiver antenna. The apparatus includes circuitry for applying radio frequency current pulses selectively to each of the plurality of transmitter antennas such that during a NMR measurement sequence while the apparatus is moving substantially only those of the plurality of transmitter antennas having radio frequency current pulses applied thereto are disposed longitudinally along a same region of interest in the subsurface formations.

A method for measuring nuclear magnetic resonance (NMR) properties of subsurface formations according to another aspect of the present disclosure includes inducing a static magnetic field in the formation for pre-polarizing nuclear spins. A plurality of radio frequency current pulses is passed through selected ones of a plurality of transmitter antennas. NMR signals are detected by at least one of the plurality of transmitter antennas and a separate receiver antenna. The selected ones of the plurality of transmitter antennas define an aperture that is substantially stationary in a frame of reference of the subsurface formations while an NMR instrument is moved along a wellbore traversing the subsurface formations.

Other aspects and advantages will be apparent from the description and claims that follow.

DETAILED DESCRIPTION

Figure 1A:
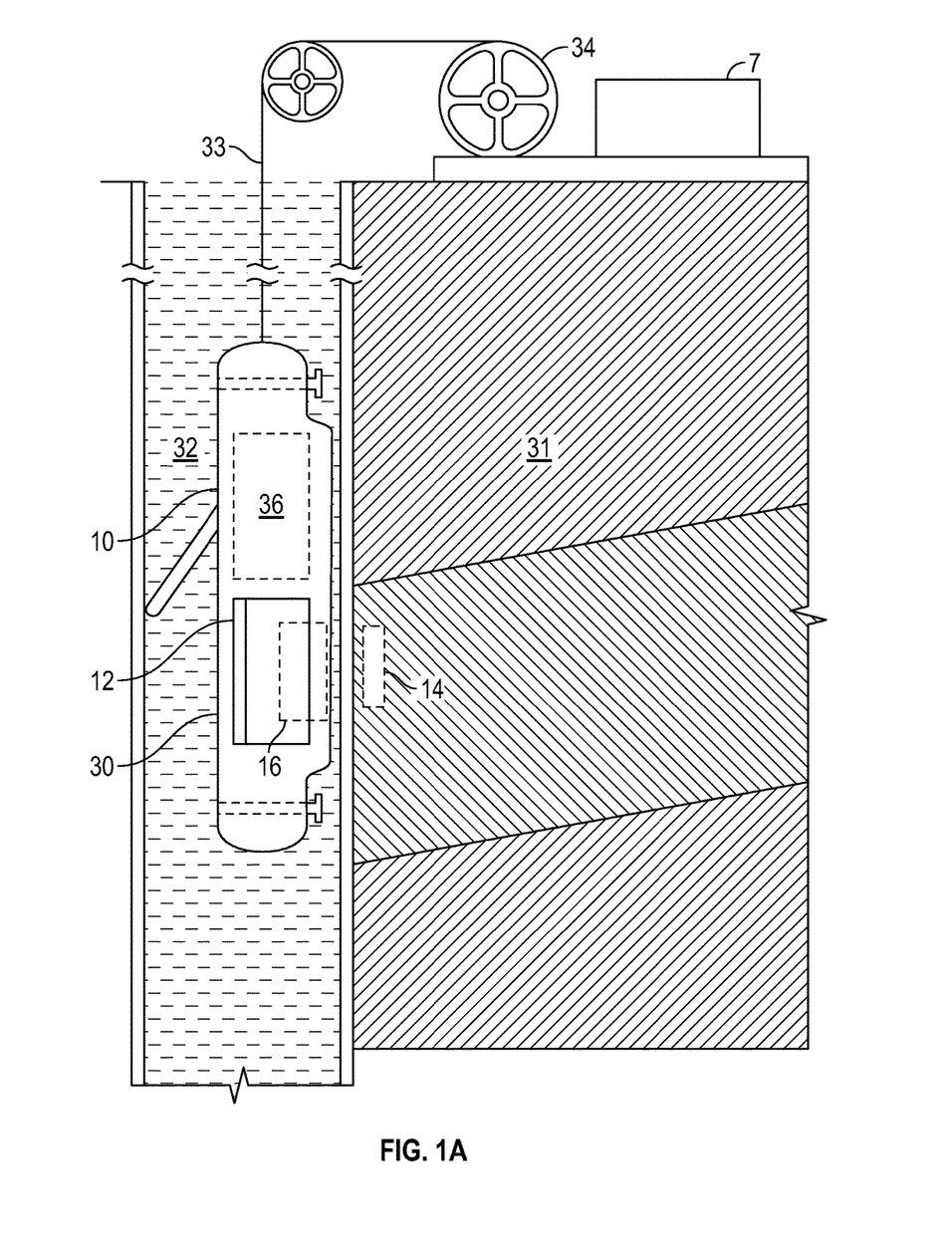
FIG. 1A shows an example wireline, slickline or coiled tubing conveyed NMR well logging instrument moving along the interior of a wellbore drilled through subsurface formations.

FIG. 1A shows an example embodiment of an apparatus 10 for investigating subsurface formations 31 penetrated by a wellbore 32, which can be made in accordance with various embodiments of a method and apparatus according to the present disclosure. The well logging instrument 10 may be suspended in the borehole 32 on an armored electrical cable 33, the length of which substantially determines the relative depth of the well logging instrument 10. The cable 33 may be extended into the wellbore 32 and withdrawn therefrom by suitable means at the surface such as a drum and winch mechanism 34. It will be appreciated that other conveyance devices for moving the well logging instrument 10 such as slickline or coiled tubing may also use a winch mechanism as shown in FIG. 1A. Surface equipment, represented at 7, can be of any type known in the art for operation well logging instruments, and may include a processor subsystem, signal communication and recording devices and a telemetry transceiver for communicating with the well logging instrument 10, whether in real time as in the case of electrical or optical cable conveyance or by other communication when conveyance other than electrical or optical cable is used.

The well logging instrument 10 which makes the measurements a NMR well logging device for use in "wireline" conveyed well logging instrumentation as shown in FIG. 1A, or of a type that can be used in logging while drilling (LWD) applications to be explained below with reference to FIG. 1B. The well logging instrument 10 includes, for example, a magnet 12 such as a permanent magnet, magnet array, electromagnet or combinations thereof for inducing a static magnetic field in the formations 31, and radio frequency (RF) antennas 16 for inducing a pulsed RF magnetic field in the formations 31 and for receiving RF energy induced by NMR phenomena excited in the formations 31 by reason of the puled RF magnetic fields induced in the formations 31. Example embodiments of such antennas will be described below in more detail with reference to FIG. 3.

The magnet 12 may have an axial dimension selected such that an axial span of the formations which is prepolarized by the static magnetic field from the magnet 12 is at least as long the distance traversed by the antennas 16 in any one or more NMR measurement sequences as the instrument 10 is moved along the wellbore 32. In some embodiments, the length of magnet 12 ahead of the antennas 16 should be long enough to prepolarize the spins. This can be accomplished by making the length of this section of the magnet 12 long compared to $vT_1max$, where $T_1max$ is the longest value of longitudinal relaxation time ($T_1$) in the formation and v represents the speed of motion of the well logging instrument 10.

The well logging instrument described above can also be implemented, for example, in logging-while-drilling ("LWD") equipment. As shown, for example, in FIG. 1B, a platform and derrick 210 are positioned over a wellbore 212 that may be formed in the Earth by rotary drilling. A drill string 214 may be suspended within the borehole and may include a drill bit 216 attached thereto and rotated by a rotary table 218 (energized by means not shown) which engages a kelly 220 at the upper end of the drill string 214. The drill string 214 is typically suspended from a hook 222 attached to a traveling block (not shown). The kelly 220 may be connected to the hook 222 through a rotary swivel 224 which permits rotation of the drill string 214 relative to the hook 222. Alternatively, the drill string 214 and drill bit 216 may be rotated from the surface by a "top drive" type of drilling rig.

Drilling fluid or mud 226 is contained in a mud pit 228 adjacent to the derrick 210. A pump 230 pumps the drilling fluid 226 into the drill string 214 via a port in the swivel 224 to flow downward (as indicated by the flow arrow 232) through the center of the drill string 214. The drilling fluid exits the drill string via ports in the drill bit 216 and then circulates upward in the annular space between the outside of the drill string 214 and the wall of the wellbore 212, as indicated by the flow arrows 234. The drilling fluid 226 thereby lubricates the bit and carries formation cuttings to the surface of the earth. At the surface, the drilling fluid is returned to the mud pit 228 for recirculation. If desired, a directional drilling assembly (not shown) could also be employed.

A bottom hole assembly ("BHA") 236 may be mounted within the drill string 214, preferably near the drill bit 216. The BHA 236 may include subassemblies for making measurements, processing and storing information and for communicating with the Earth's surface. Such measurements may correspond to those made using the NMR well logging instrument explained above with reference to FIG. 1A. The bottom hole assembly is typically located within several drill collar lengths of the drill bit 216. In the illustrated BHA 236, a stabilizer collar section 238 is shown disposed immediately above the drill bit 216, followed in the upward direction by a drill collar section 240, another stabilizer collar section 242 and another drill collar section 244. This arrangement of drill collar sections and stabilizer collar sections is illustrative only, and other arrangements of components in any implementation of the BHA 236 may be used. The need for or desirability of the stabilizer collars will depend on drilling conditions as well as on the demands of the measurement.

Figure 1B:
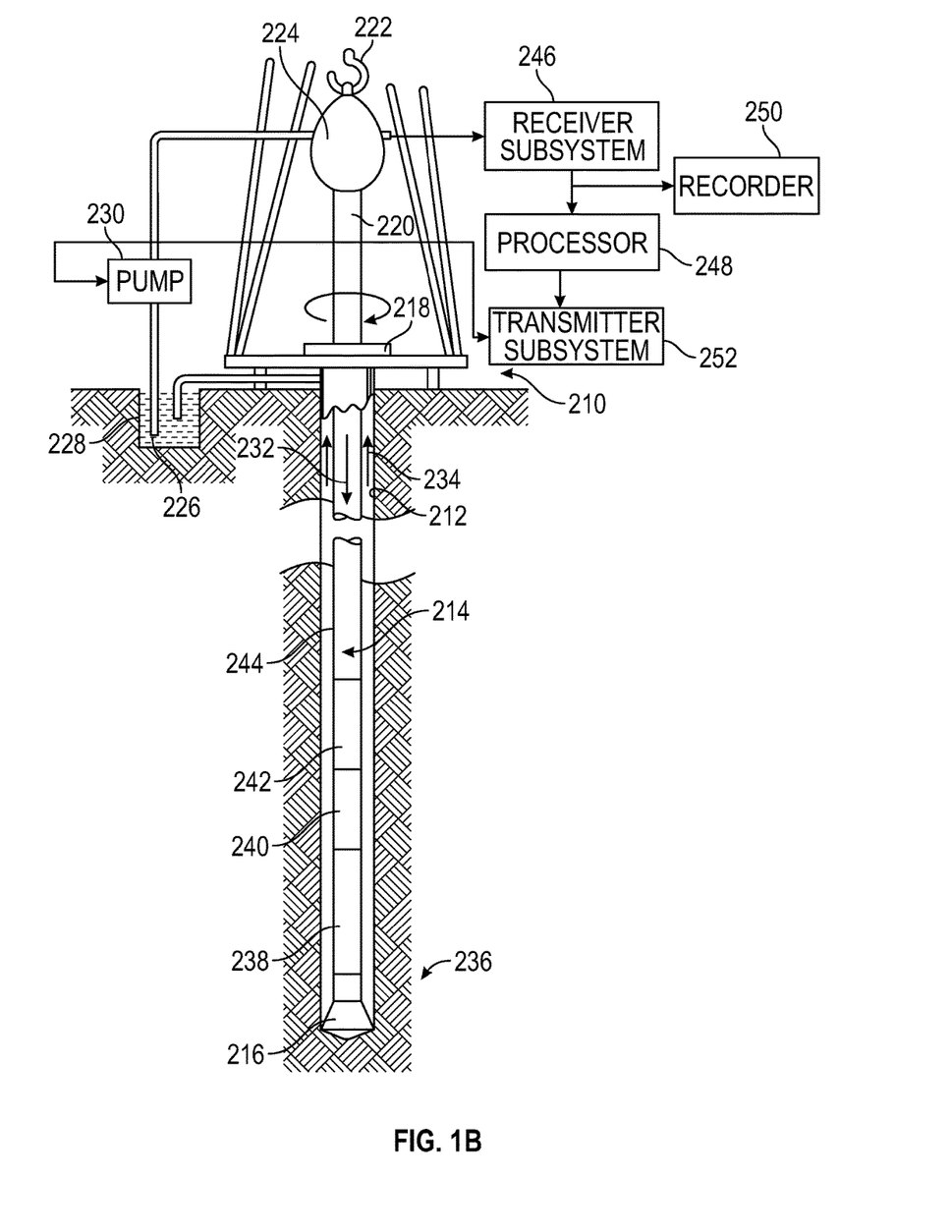
FIG. 1B shows an example logging while drilling (LWD) NMR logging instrument.

In the arrangement shown in FIG. 1B, the components of the NMR well logging instrument may be located, for example, in the drill collar section 240 above the stabilizer collar 238. Such components could, if desired, be located closer to or farther from the drill bit 216, such as, for example, in either stabilizer collar section 238 or 242 or the drill collar section 244.

The BHA 236 may also include a telemetry subassembly (not shown) for data and control communication with the Earth's surface. Such telemetry subassembly may be of any suitable type, e.g., a mud pulse (pressure or acoustic) telemetry system, wired drill pipe, etc., which receives output signals from LWD measuring instruments in the BHA 236 (including the NMR well logging instrument) and transmits encoded signals representative of such outputs to the surface where the signals are detected, decoded in a receiver subsystem 246, and applied to a processor 248 and/or a recorder 250. The processor 248 may comprise, for example, a suitably programmed general or special purpose processor. A surface transmitter subsystem 252 may also be provided for establishing downward communication with the bottom hole assembly.

The BHA 236 may also include conventional acquisition and processing electronics (not shown) comprising a microprocessor system (with associated memory, clock and timing circuitry, and interface circuitry) capable of timing the operation of the source and the data measuring sensors, storing data from the measuring sensors, processing the data and storing the results, and coupling any desired portion of the data to the telemetry components for transmission to the surface. The data may also be stored in the instrument and retrieved at the surface upon removal of the drill string. Power for the LWD instrumentation may be provided by battery or, as known in the art, by a turbine generator disposed in the BHA 236 and powered by the flow of drilling fluid. The LWD instrumentation may also include directional sensors (not shown separately) that make measurements of the geomagnetic orientation or geodetic orientation of the BHA 236 and the gravitational orientation of the BHA 236, both rotationally and axially.

The foregoing computations may be performed on a computer system such as one shown in the processor at 248 in FIG. 1B, or in the surface unit 7 in FIG. 1A. However, any computer or computers may be used to equal effect.

The well logging instrument 10 may comprise circuitry 36 for applying pulses of RF current through the antennas 16 and for detecting voltages induced in the antenna(s) 16, of the well logging instrument 10. A non-limiting example embodiment of suitable circuitry is described in U.S. Pat. No. 6,140,818, "NMR logging tool and method for fast logging", issued Oct. 31, 2000. The exact configuration of the circuitry is not intended to limit the scope of the present disclosure; those skilled in the art will be able to design different forms of suitable circuitry for use in the well logging instrument 30. The spatial distribution of the static magnetic field induced by the magnet 12 and the spatial distribution of RF magnetic fields induced by passing pulses of RF current through the antennas 16 excite NMR phenomena in a sensitive region 14. The spatial distribution of the sensitive region 16 in the formations 31 is related to the spatial distribution of the static and RF magnetic fields, and the gyromagnetic ratio γ of the nuclei being excited for NMR measurement.

Figure 2:
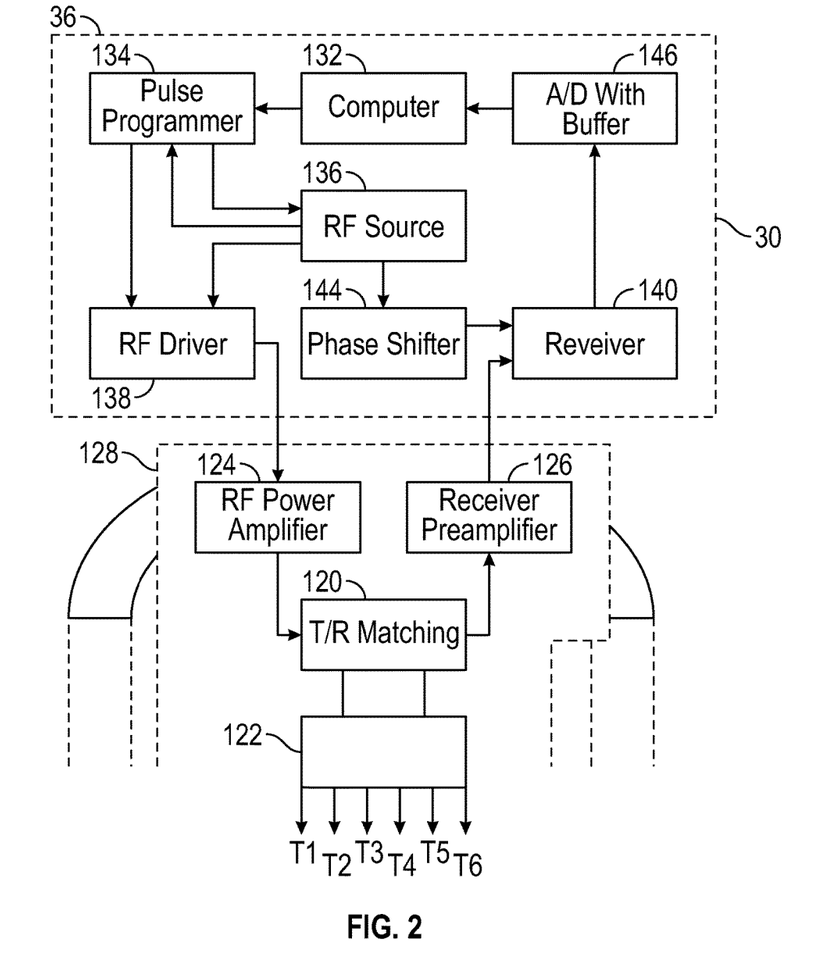
FIG. 2 shows an example embodiment of NMR measurement circuitry.

FIG. 2 shows an example of circuitry (36 in FIG. 1) that may be used in some embodiments. Individual transmitter antennas (e.g., wire coils as will be explained with reference to FIGS. 4A and 4B) T1 through T6 may be connected to a multiplexer or multiport switch 122. In some embodiments each of the antennas T1-T6 may also perform the function of a receiver antenna. In such embodiments, selected ones of the antennas T1-T6 using the multiplexer or multiport switch 122 may be electrically connected to a transmitter/receiver (T/R) matching circuit 120 defining a transmitter/receiver (T/R) circuit. The T/R matching circuit 120 may include circuit elements such as a resonance capacitor, a T/R switch and both to-transmitter and to-receiver matching circuitry. The T/R matching circuit 120 may be functionally coupled to a RF power amplifier 124 and to a receiver preamplifier 126, depending on whether the particular antenna is operating as a transmitter or as a receiver antenna. It will be appreciated that separate circuitry for each antenna T1-T6 may be substituted for the single circuit and multiplexer/switch 122. In some embodiments, one or more separate receiver antennas may be used, as will be described in more detail with reference to FIG. 4A.

Disposed in the housing indicated at 30 is example control circuitry 136 for the logging instrument including a processor or computer 132, which provides a control output to a pulse programmer 134 which receives an RF input from a RF source 136. The pulse programmer 134 controls the operation of the RF source 136 as well as an RF driver 138, which receives an input from the RF source 136 and outputs therefrom to the RF power amplifier 124.

The output of RF receiver preamplifier 126 is conducted to an RF receiver 140 which may also receive an input from a phase shifter 144. The phase shifter 144 receives an input from the RF source 136. The RF receiver 140 outputs through an A/D converter with a buffer 146 to the computer 132 for providing desired well logging output data for further use and analysis, e.g., Carr-Purcell-Meiboom-Gill (CPMG) spin echo measurements.

Figure 2A:
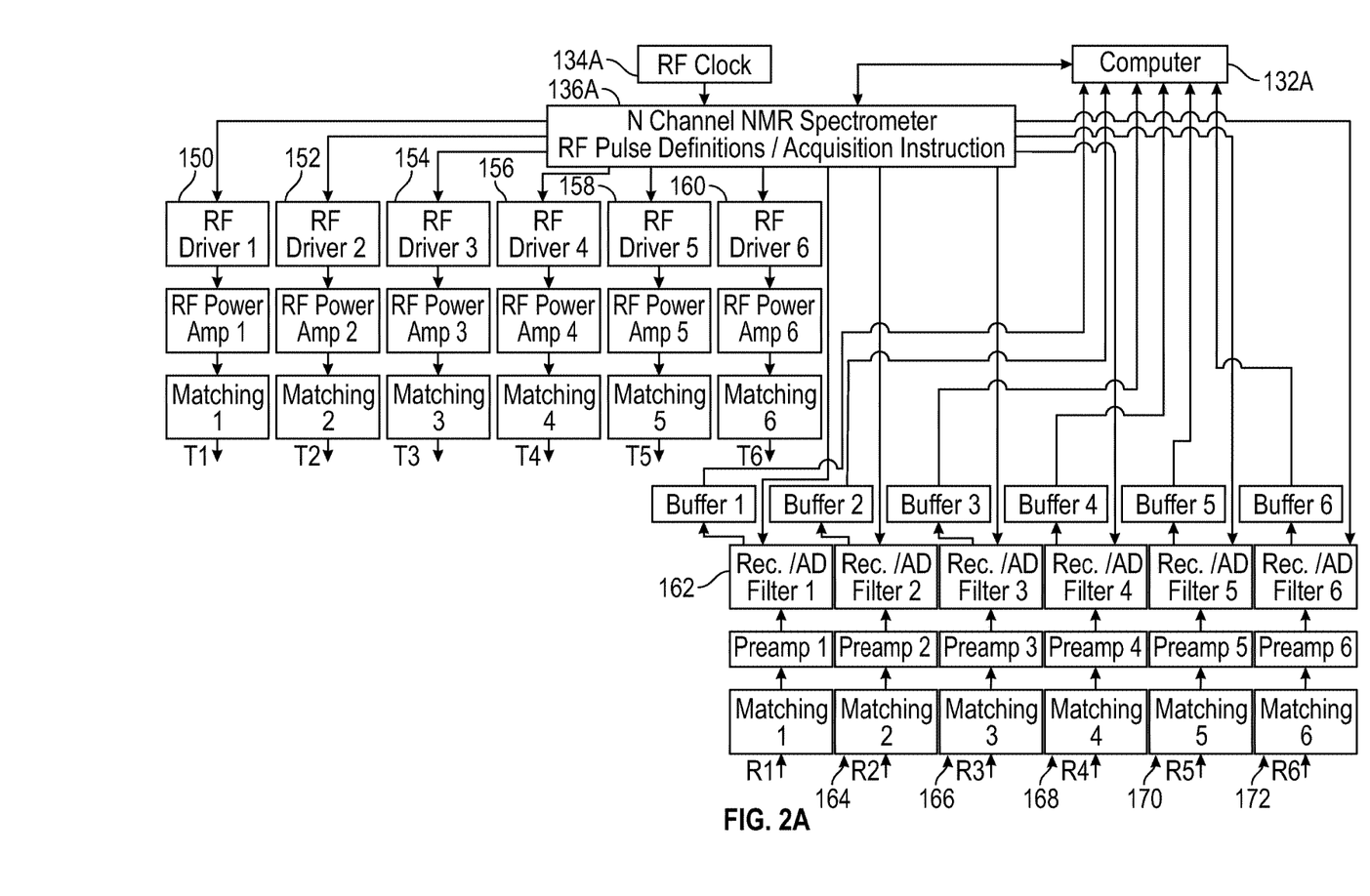
FIG. 2A shows another example embodiment of NMR measurement circuitry.

Another example embodiment of NMR measurement circuitry is shown schematically in FIG. 2A. A clock 134A may provide a timing reference for a multichannel (in the present example six channel) NMR spectrometer 136A, which determines RF pulsing sequences to be transmitted through each antenna (T1-T6). Each antenna may be actuated by a transmitter circuit, respectively shown at 150, 152, 154, 156, 158 and 160 comprising a RF driver, RF power amplifier and matching circuit. Operation of the NMR spectrometer 136A may be controlled by a computer or processor 132A.

Detecting NMR signals may comprise receiver circuitry selectively coupled to each antenna T1-T6 or to separate receiver antennas. Such receiver circuits, shown at 162, 164, 166, 168, 170 and 172 may each comprise a matching circuit, a preamplifier and analog to digital converter (Rec. AD). Output of each Rec. AD may be coupled to a respective buffer (Buffer 1 through Buffer 6) for interrogation and processing by the computer 132A or another processor.

All of the elements described hereinabove which may be contained in the housing 30 may be located either above ground or alternatively may be passed through the wellbore (32 in FIG. 1).

A measurement apparatus and method according to the present disclosure is able to compensate for relative motion between the NMR sensor and the formation during measurement. It is based on the use of multiple transmitter coils. The different transmitter coils may be activated in synchronization with the instrument movement during measurement. This leads to a new principle of a synthetic aperture that is synchronized to the instrument motion and a measurement volume that is stationary with respect to the formation during the measurement time.

Figure 3:
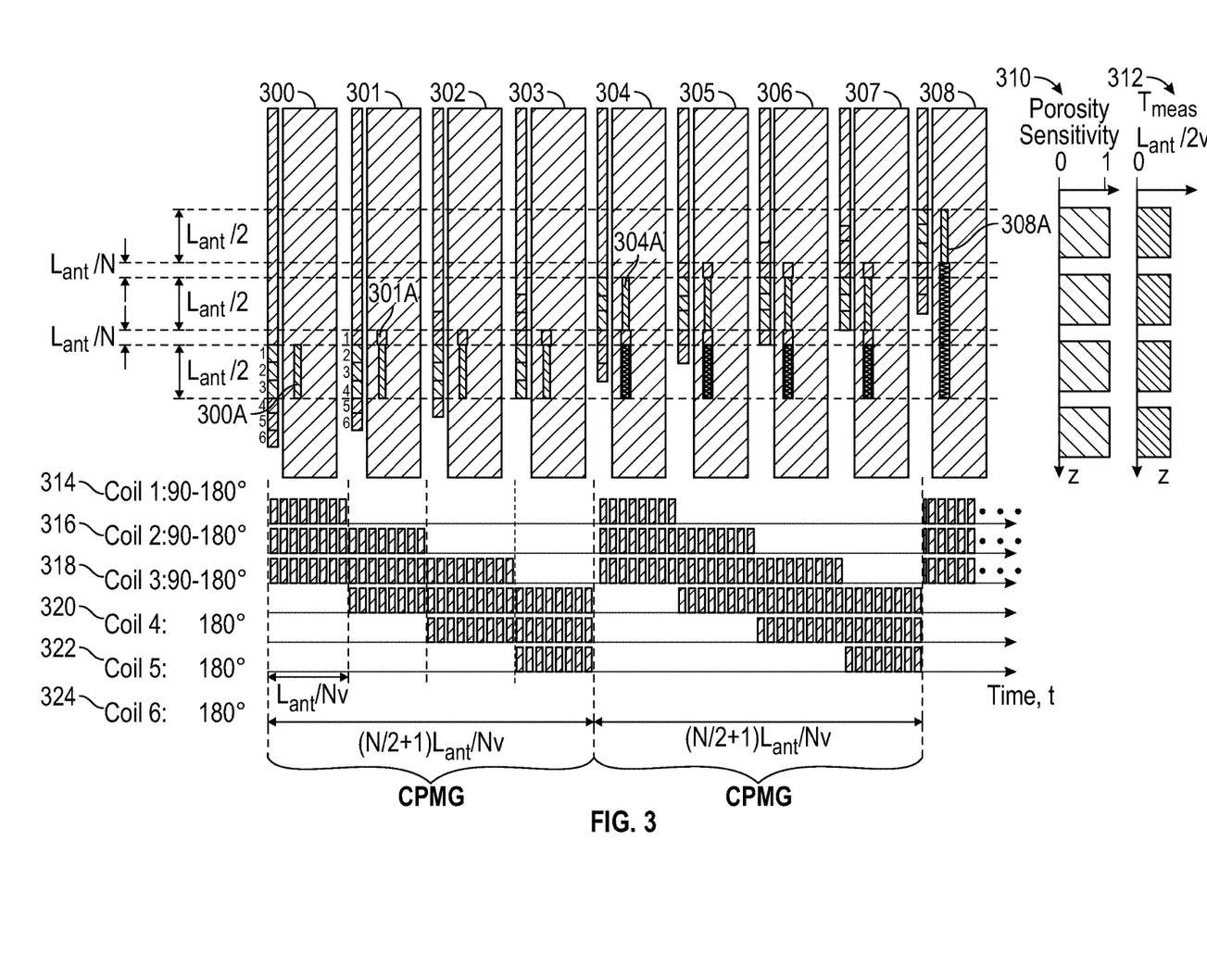
FIG. 3 shows schematically positions of a NMR well logging instrument and selective actuation of a plurality of transmitter coils.

An example embodiment of an implementation is schematically illustrated in FIG. 3. The RF transmitter in this embodiment comprises a number N of separate antennas (e.g., wire coils) that can be individually energized and controlled, for example, using the circuitry as explained with reference to FIG. 2. In the example shown in FIG. 3, N=6. The combined axial length of all N separate coils may be defined as the antenna length Lant. The position of the logging instrument is shown at nine sequential times and positions 300-308 along the interior of the wellbore. Each position 300-308 has a corresponding position of the well logging instrument shown. In the first position 300, the instrument is positioned so that the uppermost three transmitter antennas, T1, T2, T3 are adjacent a sensitive region 300A.

The sequence of RF current pulses applied to the various antennas are shown schematically below each position of the well logging instrument. At the first instrument position 300, a 90° orienting RF magnetic field pulse is emitted by each of the upper three transmitters T1, T2, T3. The foregoing RF pulse induces NMR phenomena in a sensitive region 300A within the longitudinal span of the upper three transmitter antennas T1, T2, T3. Following the 90° orienting pulse, a series of 180° refocusing RF pulses is emitted by each of the upper three transmitter antennas T1, T2, T3. When the instrument has moved to the second position 301, which represents a time interval Lant/Nv, wherein v represents the speed of motion of the logging instrument, the 180° RF pulsing to the uppermost transmitter antenna T1 is switched off. 180° refocusing RF current pulses are passed through the second and third transmitter antennas, T2 and T3, respectively, continues, and at the second position 301, 180° refocusing RF pulsing through the fourth transmitter antennas T4 begins. In the case of the second transmitter antennas T2, the 180° RF current pulsing stops when the instrument reaches the third position 302. At that time, 180° refocusing pulsing through the fifth transmitter antennas T5 begins. At the fourth position 303, 180° RF pulsing through the third transmitter antennas T3 has stopped and 180° RF current pulsing through the sixth transmitter antenna T6 begins. After the instrument moves a further distance of Lant/N, to account for the relatively small axial span 301A not exposed to the original 90° orienting pulse at the position of the first transmitter antenna T1 with the instrument at the second position 301, the foregoing sequence of applying 90° and 180° RF pulses through each of the transmitter antennas T1-T6 may be repeated. The small axial span 301A represents the hole burning region, and as may be inferred from FIG. 3, the axial span of the hole burning region 301A may be of length Lant/N as contrasted with a length Lant using a conventional single transmitter antenna. During movement of the instrument from the first position 300 to the fourth position 303, the instrument has moved a distance defined by (N/2+1) Lant/N. This distance is approximately the same as the length of the sensitive region 300, and in each case, essentially only a region of the formation that has been fully exposed to the 90° RF orienting pulse is subsequently exposed to 180° refocusing RF pulses. A repetition of the sequence shown for positions one through four (300-303) is show for positions five through eight (304-307). The ninth position 308 shows the sequence beginning for a third time with the upper three transmitter antennas T1-T3 longitudinally adjacent to a third region of interest 308A. As shown schematically at 310 and 312, the porosity sensitivity and measurement time are equal and maximized over each measurement interval by the effective aperture technique using multiple transmitters as explained herein. The pulsing sequences for each transmitter antenna T1-T6 at each position 300-308 are shown sequentially at 314, 316, 318, 320, 322 and 324 in FIG. 3.

In this example, at any time half the transmitter antennas are activated. As the instrument moves upwardly, only those of the transmitter coils T1-T6 that are in front of the range of formation that experienced the initial 90° RF magnetic field excitation pulse are activated. In this way, the effective aperture of the transmitter coils is kept stationary with respect to the formation. As a result, the porosity sensitivity and effective measurement time Tmeas are to a first order uniform across the formation. It will be appreciated that the same effect may be obtained by reversing the transmitter antenna actuation sequence shown in FIG. 3 in the case where the well logging instrument moves downwardly through the wellbore.

The present approach may be thought of as a composite transmitter coil with a synthetic aperture that can be controlled electronically. In one form, the aperture is fixed in the frame of reference of the formation during the measurement time (e.g., a CPMG pulse sequence). This effectively compensates for the instrument motion. The measurement approach does not create a large hole-burning region that prevents subsequent quantitative NMR investigation therein. In the example shown in FIG. 3, the length of the hole-burning region is reduced to Lant/N and could be further reduced by more sophisticated RF magnetic field pulse sequences.

To receive the NMR signals excited by the RF magnetic field pulses induced by the antennas T1-T6, the individual transmitter antennas may be used as receiver antennas. This may optimize the spatial resolution, which in this case becomes the (bipole) length of the individual antennas, i.e., approximately Lant/N.

In some embodiments it may be possible to use just one receiver antenna, e.g., a wire coil, of length Lant. Using a single receiver antenna has the advantage that only a single set of receiver electronics is required. However, using a single receiver antenna of the above suggested length may result in lower spatial resolution than is made possible by the NMR excitation profile generated by operating the transmitter antennas as described above. In the example shown in FIG. 3, the spatial resolution is Lant/2. This is coarser resolution than what may be obtained using N individual receiver antennas, but still better than the length of the single receiver antenna. In addition, the use of a single receiver antenna will decrease the overall signal-to-noise ratio. With a single receiver antenna, the detected signal is ideally the same as the sum of the signals detected with multiple receiver antennas, but the detected noise from the formation is $\sqrt{2}$ higher because the receiver antenna senses noise from a region that is twice as large as the region generating NMR signals.

In the example shown in FIG. 3, the transmitter antennas are energized in such a way that during the measurement time, the targeted region of the formation is uniformly magnetized with RF magnetic field and that all spins in the targeted region of the formation experience a fully magnetized RF pulsing sequence, such as a CPMG sequence. This same method may be generalized to any other type of NMR pulse sequence, including diffusion editing or $T_1$-$T_2$ sequence. It is also possible to generalize the approach and to create different types of spatial excitation profiles so that different parts of the formation experience different types of pulse sequences. To obtain such results, it may be desirable to use multiple receiver antennas. As an example, different regions can be programmed to encode different recovery times for T, measurement, or different diffusion time for fluid typing measurements based on the diffusion editing sequence. Provided that the formation is sufficiently homogeneous between the different regions, it is then possible with this multiplexing approach to combine the measurements from the different sections of the formation to extract a complete T, or diffusion measurement in much shorter time than is possible with a single transmitter coil.

In NMR well logging techniques known in the art prior to the present disclosure, the choice of the length of the antenna Lant represents a tradeoff between the effective measurement time Tmeas (that is related to resolution of the relaxation times) and the desired spatial resolution of the measurements. Using apparatus and methods as disclosed herein, Tmeas≈Lant/2v, while the spatial resolution is Lant/N. Ideally, Tmeas should be as long as possible, whereas the spatial resolution should be as short as possible. In one possible implementation such conditions may be obtained by making the total antenna length Lant as long as possible, while maximizing the number of individually controllable antenna elements or coils, N.

In FIG. 3, the spatial response of individual antennas is idealized and is indicated by simple rectangular shapes. Physically embodied antennas or coils conform to Maxwell's equations and have a less localized response than as illustrated in FIG. 3. In general, there will be some inductive coupling between nearby transmitter antennas that can complicate the implementation of the present example method, especially if all the transmitter coils are used in tuned circuits.

Following are some simple coil geometries that may be suitable for multi-transmitter implementation.

The original motivation for methods and apparatus according to the present disclosure was for fast NMR well logging. However, methods and apparatus according to the present disclosure may also provide advantages, for example, using multiple-transmitter, multiple-receiver configurations, it is possible to speed up substantially the acquisition of multi-dimensional NMR experiments, including D-$T_2$, D-$T_1$-$T_2$, or $T_1$-$T_2$ measurements and combinations of the foregoing, wherein D represents diffusion coefficient, $T_1$ represents longitudinal relaxation time and $T_2$ represents transverse relaxation time. Furthermore, by comparing the signals from different receiver coils, the measurements can be used to measure directly the local tool motion and the logging speed. When tool sticking is important, it is difficult to infer the tool motion from the motion of the cable at the surface. Using the principle of synthetic aperture that is synchronized to the tool motion, this approach is still effective when the tool is moving relative to the formation.

Figures 4A, 4B:
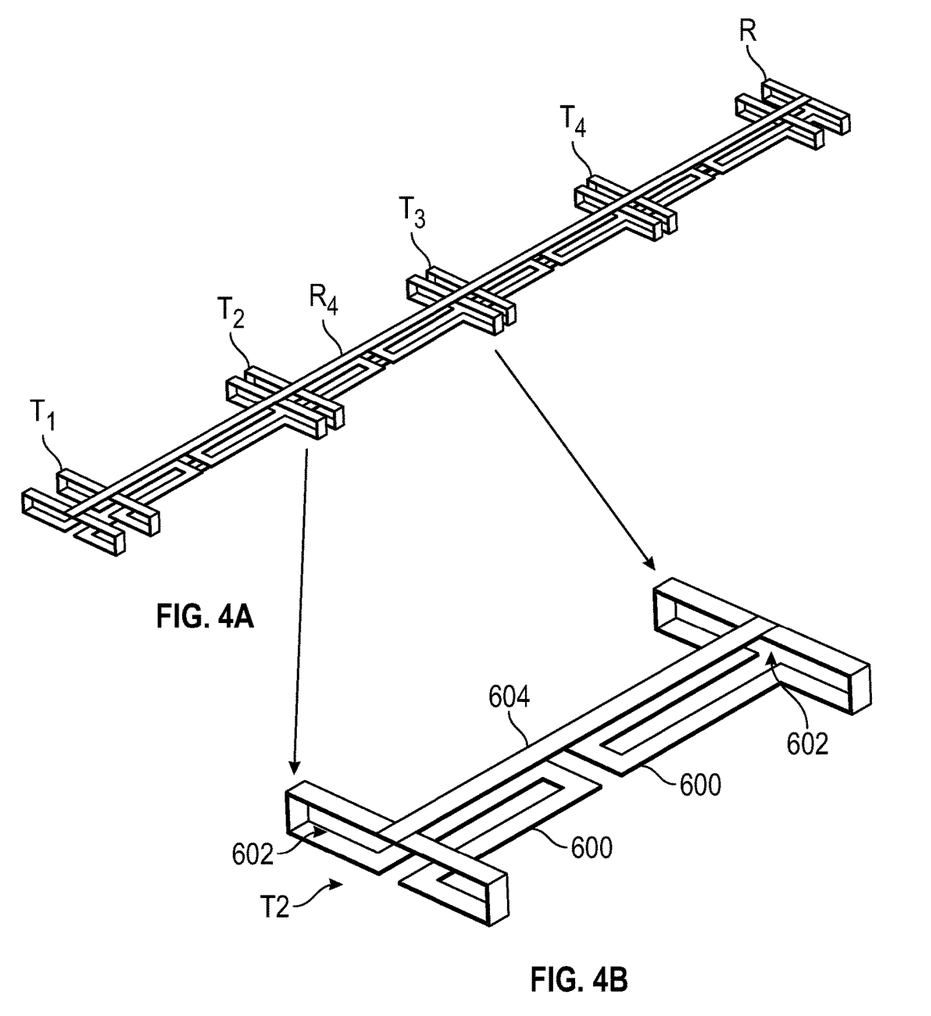
FIGS. 4A and 4B show, respectively example embodiments of a combination multiple transmitter coil and single receiver coil arrangement, and one of the transmitter coils from FIG. 4A.

A multi-transmitter antenna (coil) system may be implemented with a wide range of different antenna configurations. Coils making up the transmitter antennas can be of the same type of coils or different type of coils with individual coils having equal or non-equal dimensions. In a multi-transmitter, single-receiver implementation, multiple transmitter antennas (e.g., coils) may be used to manipulate the spins in the formation. A single receiver antenna may be used to measure the resulting signal. This configuration requires only a single set of receiver electronics, but limits somewhat the spatial resolution. An example embodiment of a multiple transmitter, single receiver combination is shown in FIG. 4A. The transmitter antennas (coils) T1, T2, T3, T4 are placed end to end and have substantially the same longitudinal end points as a separate receiver (coil) R. In some embodiments, the transmitter coils may be partially axially overlapping rather than adjacent end to end as shown in FIG. 4A.

FIG. 4B shows a single transmitter coil of the transmitter coils in FIG. 4A in more detail. The antenna coil may comprise two longitudinally spaced apart flat wire loops 602 at the longitudinal ends, an interconnecting conductor 604 that connects a center point of each wire loop 602 to the center point of the opposed wire loop 602. An electrical terminal 600 may be connected to open ends of each wire loop 602. Such arrangement of the antenna coil may be suitable for insertion into a lateral recess formed in an exterior surface of the magnet (see FIG. 1). The receiver coil (R in FIG. 4A) may be formed similarly to the transmitter coil shown in FIG. 4B, but may have an interconnecting conductor (R4 in FIG. 4A) and terminals (not shown separately) that are approximately the same length as the combined length of all the transmitter coils (T1 through T4 in FIG. 4A). In the example embodiment shown in FIGS. 4A and 4B, the number of (N) and the distance between transmitter coils T1-T4 are chosen to excite a volume sensed by the single receiver coil.

A design parameter to be considered in a multi-transmitter coil system is mutual inductive coupling between the adjacent transmitter coils due to inductive coupling. The mutual coupling between coils can be characterized by K which is the ratio of mutual inductance M to $\sqrt{L_1 L_2}$ where $L_1$ and $L_2$ are the inductances of the individual adjacent transmitter coils. The transmitter coil configuration in FIG. 5A has a mutual coupling constant, K, as low as 0.01. As a result, if 1 ampere current is conducted in to one of the transmitter coils, a 0.01 ampere current will be induced in the adjacent transmitter coil(s). This means that even when there is no current applied directly by the transmitter circuitry to the coils adjacent the coil(s) being energized, the adjacent coil(s) still contribute(s) to the overall RF magnetic field produced. While it is in principle possible to use strongly coupled transmitter coils, it is desirable to use transmitter coils with mutual coupling as small as possible. A complete knowledge of coupling constants, Ks, between the transmitter coils is theoretically sufficient to synthesize a desired RF magnetic field ($B_1$) spatial distribution with multiple transmitters. However, using strong mutual coupling approach may not be practical in well logging applications as the coupling constants are likely affected by environmental effects such as temperature and wellbore fluid salinity (electrical conductivity) variations. As a result, for robust operation, it is desirable to reduce the mutual coupling between individual coils for a multi-transmitter system as much as possible.

Furthermore, minimizing mutual coupling between transmitter coils provides additional flexibility for designing desired RF magnetic field spatial distributions from a combination of the RF magnetic fields from the magnetic field distributions resulting from each of the individual transmitter coils.

There are many other possible implementations of the multiple-transmitter single-receiver coil configuration. In the example shown in FIG. 4A, the different transmitter coils are fairly well decoupled from each other, but are strongly coupled to the receiver coil. The decoupling between the transmitter coils and the receiver coil can be improved by using a different receiver coil. As an example, a solenoid type of receiver coil is to first order decoupled from the transmitter coil by symmetry. This receiver coil can be designed to sense signals from a volume that is similar to the volume excited by the transmitter coil.

Figures 5A, 5B:
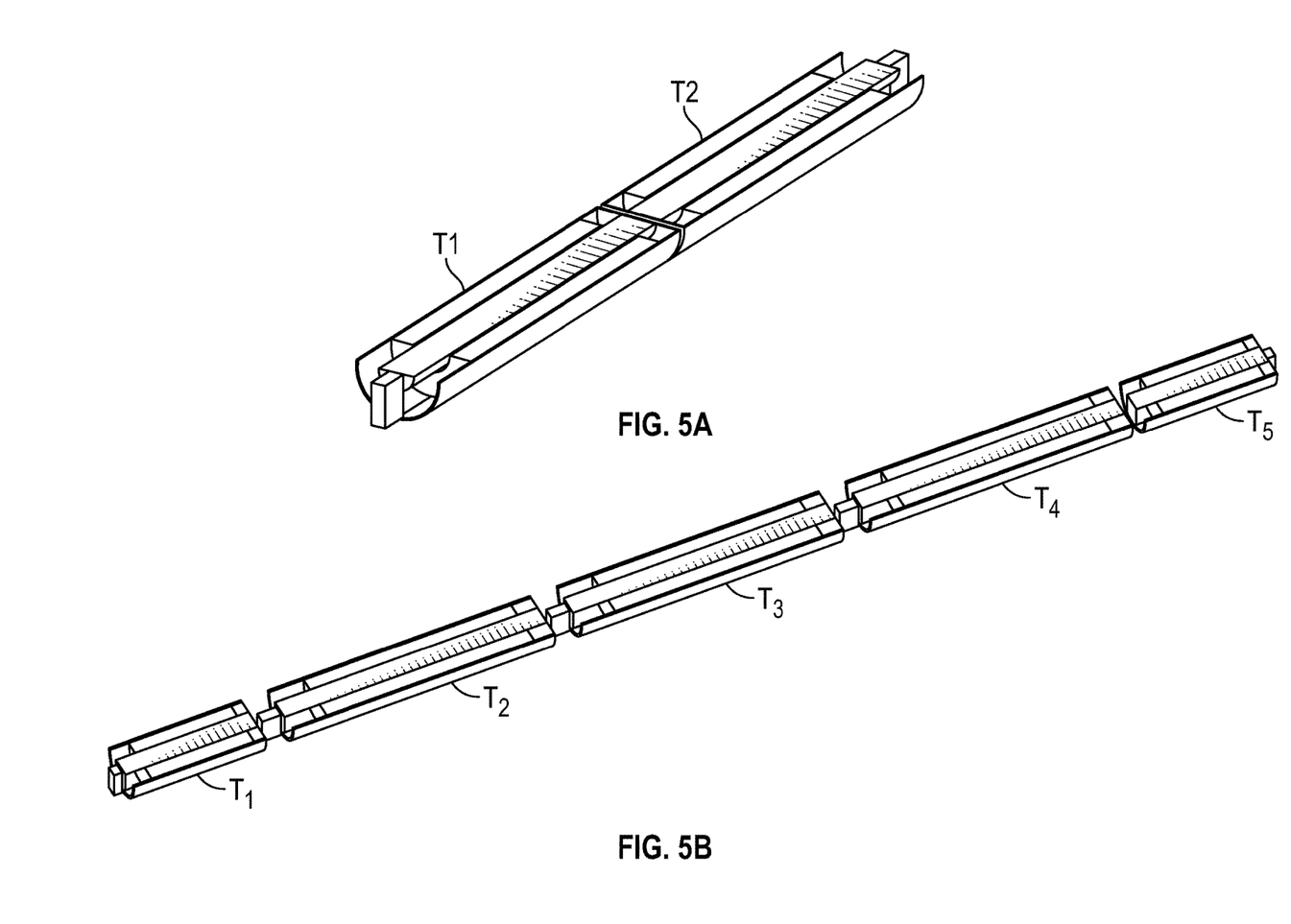
FIGS. 5A and 5B show, respectively, various example embodiments of multiple transmitter coils.

In another implementation, the same set of coils mat be used for transmit and receive. Compared to the single receiver approach, the multi-receiver approach improves the spatial resolution obtainable from the measurement, but it increases the complexity of the electronics. In this case, it is necessary to operate multiple receivers. Two examples of a multi-transmitter/receiver coil systems for this implementation are shown in FIGS. 5A and 5B. The two-coil system shown in FIG. 5A consists of two identical coils T1, T2. Each individual coil T1, T2 is used to transmit and receive. The coil configuration shown in FIG. 5A can reduce K down to 0.01.

FIG. 5B shows an antenna coil system with more than two coils. The number and the size of the individual coils can be selected as desired for optimum operation. Note that in the example shown in FIG. 5B, the longitudinal endmost end coils T1, T5 are shorter than the other coils T2, T3, T4. The endmost coils T1, T5 along with the middle three coils T2, T3, T4 can be configured to reshape the profile of the $B_1$ excitation field.

Non-ideal behavior of antenna coils, such as non-uniformity of $B_1$ across the entire sensitive region can be compensated by using more sophisticated RF pulse sequences than shown in FIG. 3. As an example, it may be advantageous to adjust the amplitudes of the individual RF pulses with respect to time and antenna (coil) position.

The example embodiments of NMR well logging instruments disclosed herein may be used with any conveyance methods, including without limitation armored electrical cable ("wireline"), on or in a well drilling assembly, (LWD), coiled tubing, downhole tractors, or slick line. Using an instrument and method according to the present disclosure, NMR logging speeds can be increased and thus save rig time. For LWD NMR instruments, the logging speeds are considerably slower than for wireline conveyed instruments, but speed effects still exist. Specifically, the sensitive region is usually axi-symmetric and short. The extent of the parasitic $T_2$ speed effect depends on the rate of penetration of the drill bit and bottom hole assembly (BHA).

In various embodiments according to the present disclosure, antenna arrangements and associated RF pulse sequences for fast NMR logging using an instrument as explained above may have one or more of the following properties: (1) substantially no $T_2$ speed effect, (2) only small longitudinal parts of the formations may be unmeasured (small hole-burning regions), (3) standard $T_2$, $T_1$ and/or diffusion based inversion methods are applicable, and (4) all measured nuclear spins are pre-polarized by a long pre-polarization magnet.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for measuring nuclear magnetic resonance (NMR) properties of subsurface formations, comprising:
   a magnet for pre-polarizing nuclear spins in the formations;
   a plurality of transmitter antennas spaced apart along a length of the apparatus;
   at least one of a receiver circuit selectively coupled to at least one of the plurality of transmitter antennas and a separate receiver antenna; and
   circuitry for applying radio frequency current pulses selectively to each of the plurality of transmitter antennas, the circuitry configured to actuate with radio frequency current pulses only those of the plurality of transmitter disposed longitudinally adjacent a same region of interest in the subsurface formations and stop the radio frequency current pulses when the transmitter antennas move out of the region of interest in the subsurface formations.

2. The apparatus of claim 1 wherein the circuitry comprises a radio frequency power amplifier coupled to a multiplexer, the multiplexer having a separate terminal connected to each of the plurality of transmitter antennas.

3. The apparatus of claim 1 wherein each transmitter antenna is selectively connected to a corresponding transmitter and receiver circuit.

4. The apparatus of claim 1 wherein the plurality of transmitter antennas comprise wire coils.

5. The apparatus of claim 4 wherein the wire coils comprise two wire loops longitudinally separated by a selected length interconnecting electrical conductor.

6. The apparatus of claim 1 wherein the plurality of transmitter antennas are configured to minimize mutual inductance therebetween.

7. The apparatus of claim 1 wherein the separate receiver antenna has a length equal to a sum of lengths of the plurality of transmitter antennas.

8. The apparatus of claim 7 wherein the separate receiver antenna comprises a wire loop separated by a selected length interconnecting electrical conductor.

9. The apparatus of claim 8 wherein a length of the interconnecting electrical conductor on the receiver antenna is substantially equal to a combined length of the plurality of transmitter antennas.

10. The apparatus of claim 1 wherein the circuitry comprises a pulse programmer configured to apply a 90 degree nuclear magnetic spin reorienting pulse through at least one of the plurality of transmitters and to apply a plurality of 180 degree nuclear magnetic spin refocusing pulses through the plurality of transmitter antennas in a selected sequence.

11. The apparatus of claim 1 wherein the circuitry selectively connects selected ones of the plurality of transmitter antennas to the receiver circuit to detect NMR phenomena induced in the subsurface formations.

12. The apparatus of claim 1 wherein the circuitry selectively applies RF current pulses through selected subsets of the plurality of transmitter antennas corresponding to motion of the apparatus and defining an aperture that is substantially stationary in a frame of reference of the subsurface formations.

13. The apparatus of claim 1 wherein the transmitter antennas have different sizes.

14. The apparatus of claim 1 wherein the plurality of transmitter antennas comprise a first end antenna located at one end of the plurality of transmitter antennas, a second end antenna located at an opposite end of the plurality of transmitter antennas, and one or more intermediate antennas located between the first end antenna and the second end antenna, and the first end antenna, the second end antenna, or both are shorter than the intermediate antennas.

15. A method for measuring nuclear magnetic resonance (NMR) properties of subsurface formations, comprising:
   inducing a static magnetic field in the formation for pre-polarizing nuclear spins;
   passing a plurality of radio frequency current pulses through selected ones of a plurality of transmitter antennas when adjacent to a region of interest in the subsurface formations;
   stopping the radio frequency current pulses in the transmitter antennas when the transmitter antennas move out of the region of interest in the subsurface formations; and
   detecting NMR signals, the detecting performed by at least one of the plurality of transmitter antennas and a separate receiver antenna, wherein the selected ones of the plurality of transmitter antennas define an aperture that is substantially stationary in a frame of reference of the subsurface formations while an NMR instrument is moved along a wellbore traversing the subsurface formations.

16. The method of claim 15 wherein the plurality of radio frequency pulses comprise a Carr-Purcell-Meiboom-Gill pulse sequence.

17. The method of claim 16 wherein the plurality of radio frequency pulses comprise a sequence for measuring at least one of a combination of $D$-$T_2$, $D$-$T_1$-$T_2$, $T_1$-$T_2$ measurements and combinations thereof, wherein D represents diffusion coefficient, $T_1$ represents longitudinal relaxation time and $T_2$ represents transverse relaxation time.

18. The method of claim 15 wherein the plurality of radio frequency current pulses have amplitude selected with respect to time and position of the selected ones of the plurality of transmitter antennas to provide a selected radio frequency magnetic field distribution in the subsurface formations.

19. The method of claim 15 wherein the selected ones of the plurality of transmitter antennas are actuated in contiguous subgroups defining an aperture that is substantially stationary in the frame of reference of the subsurface formations.

20. The method of claim 19 further comprising:
repeating the passing a plurality of radio frequency current pulses through selected ones of a plurality of transmitter antennas; and
detecting NMR signals, the detecting performed by at least one of the plurality of transmitter antennas and a separate receiver antenna, wherein the selected ones of the plurality of transmitter antennas define an aperture that is substantially stationary in a frame of reference of the subsurface formations while an NMR instrument is moved along a wellbore traversing the subsurface formations, the repeating beginning after a longitudinal endmost one of the plurality of transmitter antennas has moved beyond and end of the defined aperture to a position defining a longitudinal end of a second defined aperture in the frame of reference of the formations.

21. The method of claim 19 wherein the plurality of radio frequency current pulses comprises Carr-Purcell-Meiboom-Gill pulse sequences each having a number of refocusing pulses selected to enable movement of the NMR well logging instrument by an axial length corresponding to a time at which any of the plurality of transmitter antennas is disposed longitudinally adjacent each of the defined aperture and the second defined aperture.

22. The method of claim 15 wherein an amplitude of the plurality of radio frequency current pulses is selected with respect to time and position of the transmitter antennas to obtain a selected radio frequency magnetic field distribution in the subsurface formations.

23. The method of claim 15 wherein the detecting NMR signals using a separate receiver antenna is performed over a length substantially equal to a total length of the plurality of transmitter antennas.

* * * * *